(12) United States Patent
Erhardt et al.

(10) Patent No.: US 10,071,951 B2
(45) Date of Patent: Sep. 11, 2018

(54) LIQUID CATION EXCHANGER

(75) Inventors: Frank Erhardt, Bielefeld (DE);
Thomas Haas, Münster (DE); Martin Roos, Haltern am See (DE); Daniel Demicoli, Essen (DE); Markus Pötter, Münster (DE); Anja Schubert, Raesfeld-Erle (DE); Jan Christoph Pfeffer, Hanau (DE); Thomas Tacke, Alzenau (DE); Harald Häger, Lüdinghausen (DE); Andreas Pfennig, Kalsdorf bei Graz (AU); Marie-Dominique Przybylski-Freund, Würselen (DE)

(73) Assignee: Evonik Degussa GmbH, Essen (DE)

( * ) Notice: Subject to any disclaimer, the term of this patent is extended or adjusted under 35 U.S.C. 154(b) by 930 days.

(21) Appl. No.: 14/000,028

(22) PCT Filed: Dec. 1, 2011

(86) PCT No.: PCT/EP2011/071494
§ 371 (c)(1),
(2), (4) Date: Oct. 28, 2013

(87) PCT Pub. No.: WO2012/110126
PCT Pub. Date: Aug. 23, 2012

(65) Prior Publication Data
US 2014/0054224 A1   Feb. 27, 2014

(30) Foreign Application Priority Data
Feb. 16, 2011   (EP) .................................... 11154707

(51) Int. Cl.
*B01D 11/00* (2006.01)
*B01J 39/04* (2017.01)
(Continued)

(52) U.S. Cl.
CPC .......... *C07C 67/62* (2013.01); *B01D 11/0492* (2013.01); *B01J 39/04* (2013.01);
(Continued)

(58) Field of Classification Search
CPC ..... B01D 11/00; B01D 11/04; B01D 11/0462; B01D 37/00; B01D 11/0492; C02F 1/26;
(Continued)

(56) References Cited

U.S. PATENT DOCUMENTS 4,661,606 A    4/1987   Tuominen et al.
5,248,720 A    9/1993   Deguchi et al.
(Continued)

FOREIGN PATENT DOCUMENTS

DE    199 19 490 A1    11/2000
JP    54-55530 A       5/1979
(Continued)

OTHER PUBLICATIONS

1998, Whalley et al., WO1998002411, A Process for the Separation of Amino Acids and Their Salts From an Aqueous Solution, PDF.*
(Continued)

*Primary Examiner* — Allison G Fitzsimmons
(74) *Attorney, Agent, or Firm* — Oblon, McClelland, Maier & Neustadt, L.L.P.

(57) ABSTRACT

The present application relates to a process for removing an organic compound having one or more positive charges from an aqueous solution, comprising the steps a) provision of the aqueous solution comprising the organic compound and of a hydrophobic organic solution which comprises a liquid cation exchanger, where the liquid cation exchanger is hydrophobic, and where the liquid cation exchanger has one or more negative charges and an overall negative charge, b)
(Continued)

contacting the aqueous solution and the organic solution, and c) separating off the organic solution from the aqueous solution.

10 Claims, 8 Drawing Sheets

(51) Int. Cl.

| | | |
|---|---|---|
| C07C 67/62 | (2006.01) | |
| B01D 11/04 | (2006.01) | |
| B01J 39/16 | (2017.01) | |
| C07C 227/40 | (2006.01) | |
| C07C 229/08 | (2006.01) | |
| C02F 1/26 | (2006.01) | |
| C02F 1/42 | (2006.01) | |
| C02F 101/34 | (2006.01) | |

(52) U.S. Cl.
CPC ............ *B01J 39/16* (2013.01); *C07C 227/40* (2013.01); *C07C 229/08* (2013.01); *C02F 1/26* (2013.01); *C02F 2001/425* (2013.01); *C02F 2101/34* (2013.01)

(58) Field of Classification Search
CPC ........ C02F 1/40; C02F 1/42; C02F 2001/425; C02F 2101/30; C02F 2101/38; C02F 2305/04; C02F 1/58; B01J 39/04; B01J 39/16; C07C 227/40; C07C 229/08
USPC ........ 210/634, 635, 638, 643, 660, 681, 799
See application file for complete search history.

(56) References Cited

U.S. PATENT DOCUMENTS

| | | |
|---|---|---|
| 6,171,501 B1 | 1/2001 | Eyal et al. |
| 6,620,970 B2 | 9/2003 | Schiffer et al. |
| 6,639,108 B2 | 10/2003 | Schiffer et al. |
| 6,764,671 B2 | 7/2004 | Haas et al. |
| 6,793,825 B2 * | 9/2004 | Maass .................. B01D 61/246 210/639 |
| 6,861,540 B2 | 3/2005 | Herwig et al. |
| 6,878,836 B2 | 4/2005 | Haas et al. |
| 7,005,528 B2 | 2/2006 | Haas et al. |
| 7,030,052 B2 | 4/2006 | Stochniol et al. |
| 7,049,450 B2 | 5/2006 | Hofen et al. |
| 7,091,384 B2 | 8/2006 | Jaeger et al. |
| 7,507,862 B2 | 3/2009 | Stochniol et al. |
| 7,879,938 B2 | 2/2011 | Häger et al. |
| 8,399,658 B2 | 3/2013 | Hengstermann et al. |
| 8,404,470 B2 | 3/2013 | Thum et al. |
| 8,445,720 B2 | 5/2013 | Hannen et al. |
| 8,703,451 B2 | 4/2014 | Haas et al. |
| 8,703,993 B2 | 4/2014 | Hannen et al. |
| 8,809,576 B2 | 8/2014 | Schraven et al. |
| 8,835,691 B2 | 9/2014 | Klasovsky et al. |
| 8,946,463 B2 | 2/2015 | Klasovsky et al. |
| 8,981,159 B2 | 3/2015 | Klasovsky et al. |
| 8,999,684 B2 | 4/2015 | Poetter et al. |
| 9,000,223 B2 | 4/2015 | Micoine et al. |
| 2002/0087036 A1 | 7/2002 | Haas et al. |
| 2003/0212298 A1 | 11/2003 | Brasse et al. |
| 2010/0068773 A1 | 3/2010 | Marx et al. |
| 2010/0266518 A1 | 10/2010 | Springer et al. |
| 2010/0291644 A1 | 11/2010 | Marx et al. |
| 2010/0324257 A1 | 12/2010 | Karau et al. |
| 2011/0118433 A1 | 5/2011 | Pötter et al. |
| 2011/0118504 A1 | 5/2011 | Haas et al. |
| 2011/0171702 A1 | 7/2011 | Reinecke et al. |
| 2011/0251399 A1 | 10/2011 | Dingerdissen et al. |
| 2012/0034665 A1 | 2/2012 | Haas et al. |
| 2012/0158020 A1 | 6/2012 | Crockett et al. |
| 2012/0315366 A1 | 12/2012 | Zehnacker et al. |
| 2013/0052700 A1 | 2/2013 | Poetter et al. |
| 2013/0164797 A1 | 6/2013 | Gielen et al. |
| 2013/0165672 A1 | 6/2013 | Klasovsky et al. |
| 2013/0165685 A1 | 6/2013 | Hannen et al. |
| 2014/0039071 A1 | 2/2014 | Thum et al. |
| 2014/0141478 A1 | 5/2014 | Schaffer et al. |
| 2014/0178948 A1 | 6/2014 | Schaffer et al. |
| 2015/0010968 A1 | 1/2015 | Engel et al. |
| 2015/0044744 A1 | 2/2015 | Pfeffer et al. |
| 2015/0111253 A1 | 4/2015 | Schaffer et al. |

FOREIGN PATENT DOCUMENTS

| | | |
|---|---|---|
| JP | 2-102261 A | 4/1990 |
| WO | WO 98/02411 | 1/1998 |
| WO | WO 2008/148640 A1 | 12/2008 |
| WO | WO 2011/036000 A1 | 3/2011 |
| WO | WO 2011/157573 A2 | 12/2011 |
| WO | WO 2012/004069 A1 | 1/2012 |
| WO | WO 2012/031884 A1 | 3/2012 |
| WO | WO 2012/110124 A1 | 8/2012 |
| WO | WO 2012/110125 A1 | 8/2012 |
| WO | WO 2012/171666 A1 | 12/2012 |
| WO | WO 2013/011018 A1 | 1/2013 |
| WO | WO 2013/020839 A1 | 2/2013 |
| WO | WO 2013/024111 A1 | 2/2013 |
| WO | WO 2013/024114 A2 | 2/2013 |

OTHER PUBLICATIONS

U.S. Appl. No. 14/000,067, filed Aug. 16, 2013, Erhardt, et al.
International Search Report dated May 3, 2012 in Application No. PCT/EP2011/071494.
Diana M. Temple, et al., "Liquid Ion-exchange Extraction of some Physiologically Active Amines", Nature, vol. 209, No. 5024, Feb. 12, 1966, pp. 714-715.
U.S. Appl. No. 14/126,607, filed Dec. 16, 2013, Haas, et al.
U.S. Appl. No. 14/380,483, filed Aug. 22, 2014, Schiemann, et al.
U.S. Appl. No. 14/367,610, filed Jun. 20, 2014, Haas, et al.
U.S. Appl. No. 14/435,339, filed Apr. 13, 2015, Engel, et al.
U.S. Appl. No. 14/419,580, filed Feb. 4, 2015, Erhardt, et al.
U.S. Appl. No. 14/238,576, filed Feb. 12, 2014, Schaffer, et al.
U.S. Appl. No. 14/238,591, filed Feb. 12, 2014, Schaffer, et al.
U.S. Appl. No. 14/233,505, filed Jan. 17, 2014, Poetter, et al.
U.S. Appl. No. 14/237,121, filed Feb. 4, 2014, Haas, et al.
U.S. Appl. No. 14/649,414, filed Jun. 3, 2015, Schaffer et al.
U.S. Appl. No. 14/763,378, Jul. 24, 2015, Haas, et al.
Dai Youyuan, et al., "Techniques for complexing and extracting organics", A Chinese Tool Book, Jul. 31, 2007, pp. 1-3 (submitting English translation only).

* cited by examiner

LIQUID CATION EXCHANGER

The present application relates to a process for removing an organic compound having one or more positive charges from an aqueous solution, comprising the steps a) providing the aqueous solution containing the organic compound and a hydrophobic organic solution which comprises a liquid cation exchanger, where the liquid cation exchanger is hydrophobic, and where the liquid cation exchanger has one or more negative charges and an overall negative charge, b) contacting the aqueous solution and the organic solution, and c) separating off the organic solution from the aqueous solution, where the liquid cation exchanger is a fatty acid, and where the organic compound has at least two amino groups and no negatively charged functional group, as well as corresponding reaction mixtures.

A fundamental problem in the biotechnological production of fine chemicals starting from renewable raw materials, said chemicals being conventionally synthesized starting from fossil fuels, consists in transferring the product first obtained, which is typically in the form of a large-volume aqueous phase, to an organic phase. This transfer is carried out firstly in order to concentrate a finished intermediate or end product and in order, if appropriate, to permit the synthetic processing in subsequent reaction steps in organic solution, secondly in order to improve the yield of the reaction in the aqueous phase by removing the desired product or to allow the reaction to proceed at all within an industrially useful framework. Direct thermal concentration of the product that is often present in low concentrations from the large-volume aqueous solution is generally not appropriate.

Partitioning a compound in a two-phase system comprising an aqueous, hydrophilic phase and an organic, hydrophobic phase which are immiscible, depends substantially on the physicochemical properties of the particular compound. Whereas compounds with a high fraction of, or exclusively consisting, of unsubstituted hydrocarbons accumulate predominantly in the hydrophobic phase, compounds with a high fraction of polar groups such as heteroatom-containing functionalities and very particularly compounds with charges are present predominantly or virtually exclusively in the aqueous phase, which hinders transfer to an organic phase.

Partitioning a compound in said two-phase system by adjusting the equilibrium is often described with the help of partition coefficients, for example according to the Nernst equation.

$$\alpha = c_{Phase\ 1}/c_{Phase\ 2},$$

A specific partition coefficient is $K_{ow}$, also referred to as P value, which characterizes the partition equilibrium of a compound between an octanol phase and an aqueous phase:

$$K_{ow} = P = c_{octanol}/C_{water}$$

One example of a positively charged organic compound that is in high demand industrially is 12-aminolauric acid (ALS) and derivatives thereof, in particular the methyl ester (ALSME). ALS is an important starting material in the production of polymers, for example for producing piping systems and nylon. Conventionally, ALS is produced starting from fossil raw materials in a process with a low yield via laurolactam, which is synthesized by trimerization of butadiene, subsequent hydrogenation with the formation of cyclododecane, subsequent oxidation to give cyclododecanone, conversion with hydroxylaurin and subsequent Beckmann rearrangement. A promising route for the biotechnological production of ALS or ALSME is described in DE10200710060705.

The prior art teaches the obtainment of positively charged organic compounds by contacting an aqueous reaction mixture comprising a biological agent with an organic phase comprising an organic solvent. Thus, for example, DE10200710060705 describes the obtainment of the product ALSME by means of extraction by shaking with ethyl acetate from an aqueous reaction mixture. Asano et al. (2008) disclose the extraction of ALS with toluene from an aqueous reaction solution comprising an ALS synthesizing enzyme.

The object of the present invention is therefore to develop a process for removing positively charged organic compounds having at least one positive charge from an aqueous reaction mixture, where as advantageous as possible a position of the partition equilibrium between reaction mixture and a hydrophobic organic phase used as extractant is desired, i.e. the partition equilibrium should as far as possible be on the side of the hydrophobic organic phase.

It is a further object of the invention to develop a process for removing organic compounds having at least one positive charge from an aqueous solution comprising a biological agent using a hydrophobic organic phase as extractant, in which the partition equilibrium is as far as possible on the side of the hydrophobic organic phase.

It is a further object of the invention to develop a process for removing organic compounds having at least one positive charge from an aqueous solution using a hydrophobic organic solution as extractant, which adversely affects and/or slows as little as possible the growth of biotechnologically relevant microorganisms, in particular *Escherichia coli*, and/or in so doing reduces the number of divisible and/or viable and/or respiratorally active cells by as little as possible.

Finally, the object of the invention is to discover a process for removing an organic compound having at least one positive charge from an aqueous solution comprising a biological agent using a hydrophobic organic phase as extractant, in which the totality of the properties that are decisive for the yield, the overall conversion and rapid practicability of an underlying biotechnological synthesis process, in particular the toxicity organic phase compared with the biological agent and the absorption of the compound into the organic extractant, is optimized with regard to the total yield or a more rapid progression or, in the case of a continuous process, as long as possible a usability of the biological agent, particularly when the organic compound having at least one positive charge is the product or an intermediate of the synthesis process which is synthesized with participation of a catalytic activity of the biological agent.

These and other objects are achieved by the subject matter of the present application and in particular also by the subject matter of the attached independent claims, with embodiments arising from the dependent claims.

The problem addressed by the invention is solved in a first aspect by a process for removing an organic compound having one or more positive charges from an aqueous solution, comprising the steps
a) providing the aqueous solution containing the organic compound and a hydrophobic organic solution which comprises a liquid cation exchanger,
where the liquid cation exchanger is hydrophobic, b) contacting the aqueous solution and the organic solution, and
c) separating off the organic solution from the aqueous solution,
where the liquid cation exchanger is a fatty acid,
and where the organic compound has at least two amino groups and no negatively charged functional group.

In a first embodiment of the first aspect of the present invention, the temperature in step b) is 28 to 70, preferably 30 to 37° C.

In a second embodiment of the first aspect of the present invention, which is also an embodiment of the first embodiment of the present invention, the pH in step b) is 6 to 8, preferably 6.2 to 7.2.

In a third embodiment of the first aspect of the present invention, which is also an embodiment of the first to second embodiment of the present invention, the problem is solved by a process, where the organic compound is a compound of the Formula $H_2N\text{—}(CH_2)_x\text{—}NH_2$, and x is 1 to 20, preferably 6 to 10.

In a fourth embodiment of the first aspect of the present invention, which is also an embodiment of the first to third embodiment of the present invention, the problem is solved by a process, where the organic diamine is a cyclic sugar having at least two amino groups, preferably diaminoisoiditol and diaminoisosorbitol.

In a fifth embodiment of the first aspect of the present invention, which is also an embodiment of the first to fourth embodiment of the present invention, the problem is solved by a process where the quantitative ratio of liquid cation exchanger to organic compound is at least 1.

In a sixth embodiment of the first aspect of the present invention, which is also an embodiment of the first to fifth embodiment of the present invention, the problem is solved by a process where the volume ratio of organic solution to aqueous solution is 1:10 to 10:1.

In a seventh embodiment of the first aspect of the present invention, which is also an embodiment of the first to sixth embodiment of the present invention, the problem is solved by the process where the liquid cation exchanger is a fatty acid having more than 12, preferably having 14 to 22, even more preferably 16 to 18, carbon atoms.

In an eighth embodiment of the first aspect of the present invention, which is also an embodiment of the first to seventh embodiment of the present invention, the problem is solved by a process where the liquid canon exchanger is an unsaturated fatty acid, preferably oleic acid or erucic acid.

In a ninth embodiment of the first aspect of the present invention, which is also an embodiment of the first to seventh embodiment of the present invention, the problem is solved by a process where the aqueous solution furthermore comprises a biological agent with catalytic activity.

In a tenth embodiment of the first aspect of the present invention, which is also an embodiment of the first to ninth embodiment of the present invention, the problem is solved by a process where the biological agent is a cell, preferably a bacterial cell.

In an eleventh embodiment of the first aspect of the present invention, which is also an embodiment of the first to tenth embodiment of the present invention, the problem is solved by a process where the organic compound is an organic compound that is toxic to the cell.

In a twelfth embodiment of the first aspect of the present invention, which is also an embodiment of the first to eleventh embodiment of the present invention, the problem is solved by a process where the organic solution moreover comprises at least one organic solvent, preferably a fatty acid and/or a fatty acid ester.

The object of the invention is achieved in a second aspect by a reaction mixture comprising an aqueous solution and a hydrophobic organic solution,
where the hydrophobic organic solution comprises a fatty acid, more preferably a fatty acid having more than 12 or 14 to 22 or 16 to 18 carbon atoms, even more preferably an unsaturated fatty acid as liquid cation exchanger,
and where the aqueous solution comprises an organic compound which has at least two amino groups and no negatively charged functional group.

In a first embodiment of the second aspect of the present invention, the problem is solved by a, where the aqueous solution further comprises an intact cell with catalytic activity, preferably a bacterial cell, more preferably *E. coli*.

In a second embodiment of the second aspect of the present invention, which is also an embodiment of the first embodiment of the present invention, the problem is solved by a reaction mixture according to one of claims 14 to 15, where the organic compound is a compound of the Formula $H_2N\text{—}(CH_2)_x\text{—}NH_2$, and x is 1 to 20, preferably 6 to 10.

In a third embodiment of the second aspect of the present invention, which is also an embodiment of the first to second embodiment of the present invention, the problem is solved by a reaction mixture, where the organic diamine is a cyclic sugar having at least two amino groups, preferably diaminoisoiditol and diaminoisosorbitol.

The object of the invention is achieved in a third aspect by a process for removing an organic compound having one or more positive charges from an aqueous solution, comprising the steps:
a) provision of the aqueous solution containing the organic compound and of a hydrophobic organic solution which comprises a liquid cation exchanger,
where the liquid cation exchanger is hydrophobic, and where the liquid cation exchanger has one or more negative charges and an overall negative charge,
b) contacting the aqueous solution and the organic solution, and
c) separating off the organic solution from the aqueous solution.

In one embodiment of the third aspect of the present invention, which is also an embodiment of the first embodiment of the present invention, the process comprises the step:
d) working-up the organic solution, preferably by back-extraction of the organic compound into a further aqueous solution.

In a second embodiment of the third aspect of the present invention, which is also an embodiment of the first embodiment of the present invention, the temperature in step b) of the process according to the invention is 28 to 70° C., preferably 30 to 37° C.

In a third embodiment of the third aspect of the present invention, which is also an embodiment of the first to second embodiment of the present invention, the pH in step b) of the process according to the invention is 3 to 8, preferably 6 to 8, particularly preferably 6.2 to 7.2.

In a fourth embodiment of the third aspect of the present invention, which is also an embodiment of the first to third embodiment of the present invention, the quantitative ratio of liquid cation exchanger to organic compound during the process is at least 1.

In a fifth embodiment of the third aspect of the present invention, which is also an embodiment of the first to fourth embodiment of the present invention, the volume ratio of organic solution to aqueous solution is 1:10 to 10:1.

In a sixth embodiment of the third aspect of the present invention, which is also an embodiment of the first to fifth embodiment of the present invention, the organic compound has at least one positively charged substituent of the Formula (I)

$$—N'R^2R^3R^4 \qquad (I)$$

or, if at least one substituent from the group comprising $R^2$, $R^3$ and $R^4$ is hydrogen, the unprotonated form thereof,
where $R^2$, $R^3$ and $R^4$, independently of one another, are selected from the group comprising hydrogen, methyl, ethyl, propyl, 2-propyl, butyl, t-butyl, pentyl, hexyl, benzyl, hydroxyl, substituted or unsubstituted and/or straight-chain or branched or cyclic alkyl or alkenyl.

In a seventh embodiment of the third aspect of the present invention, which is also an embodiment of the first to sixth embodiment of the present invention, the organic compound has the Formula (II)

$$Z-A-N^+R^2R^3R^4 \qquad (II)$$

or, if at least one substituent from the group comprising $R^2$, $R^3$ and $R^4$, is hydrogen, the unprotonated form thereof,
where $R^2$, $R^3$ and $R^4$, independently of one another, are selected from the group comprising hydrogen, methyl, ethyl, propyl, 2-propyl, butyl, t-butyl, pentyl, hexyl, benzyl, hydroxyl, substituted or unsubstituted and/or straight-chain or branched or cyclic alkyl or alkenyl,
where A is a hydrocarbon chain comprising at least three carbon atoms, preferably an unsubstituted alkenyl group,
and where Z is selected from the group which comprises —COOH, —COOR⁵, —COH, —CH₂OH and unprotonated forms thereof,
where $R^5$ is selected from the group comprising hydrogen, methyl, ethyl, propyl, 2-propyl, butyl, t-butyl, pentyl, hexyl, benzyl, hydroxyl, substituted or unsubstituted and/or straight-chain or branched or cyclic alkyl or alkenyl.

In an eighth embodiment of the third aspect of the present invention, which is also an embodiment of the first to seventh embodiment of the present invention, the organic compound has the Formula III $$NH_3^+-A-COOR^1 \qquad (III).$$

or an unprotonated form thereof, where $R^1$ is hydrogen, methyl or ethyl and A is an unsubstituted, straight-chain alkylene group having at least three carbon atoms.

In a ninth embodiment of the third aspect of the present invention, which is also an embodiment of the first to eighth embodiment of the present invention, the liquid cation exchanger has at least one alkyl or alkenyl group having at least six carbon atoms, and also a terminal substituent from the group which comprises —COOH, —OSO₂H, —OPO(OH)₂— and —OPO(OH)O— and unprotonated forms thereof.

In a tenth embodiment of the third aspect of the present invention, which is also an embodiment of the first to ninth embodiment of the present invention, the liquid cation exchanger is an unsaturated fatty acid, preferably oleic acid.

In an eleventh embodiment of the third aspect of the present invention, which is also an embodiment of the first to tenth embodiment of the present invention, the aqueous solution furthermore comprises a biological agent with catalytic activity.

In a twelfth embodiment of the third aspect of the present invention, which is also an embodiment of the first to eleventh embodiment of the present invention, the biological agent is a cell, preferably a bacterial cell.

In a fourteenth embodiment of the third aspect of the present invention, which is also an embodiment of the first to twelfth embodiment of the present invention, the presence of the organic compound has a disadvantageous effect on the catalytic activity.

In a fifteenth embodiment of the third aspect of the present invention, which is also an embodiment of the first to thirteenth embodiment of the present invention, the organic solution moreover comprises at least one organic solvent, preferably a fatty acid and/or a fatty acid ester.

In a sixteenth embodiment of the third aspect of the present invention, which is also an embodiment of the first to fourteenth embodiment of the present invention, the organic solution comprises, as liquid cation exchanger, 20 to 80% by volume, preferably 25 to 75% by volume, of oleic acid, and, as solvent, lauric acid methyl ester and the organic compound is methyl 12-aminolaurate, and a bacterial cell which has catalytic activity involved in the synthesis of methyl 12-aminolaurate is present in the aqueous solution.

In a seventeenth embodiment of the third aspect of the present invention, which is also an embodiment of the first to fifteenth embodiment of the present invention, the organic compound is a cyclic sugar with at least one amino group, preferably with at least two amino groups.

In a fourth aspect, the object of the invention is solved by a bioreactor comprising an aqueous solution, comprising a biological agent, and a hydrophobic organic solution comprising a liquid cation exchanger. In a preferred embodiment of the present invention, the term "bioreactor", as used herein, is understood as meaning the vessel in which biotechnologically useful microorganisms are cultured under controlled conditions and/or can be used for a biotechnological process, preferably the synthesis of an organic compound.

In a first embodiment of the fourth aspect, which is also an embodiment of the first embodiment of the third aspect of the present invention, the liquid cation exchanger is a fatty acid, preferably oleic acid.

In a second embodiment of the fourth aspect, which is also an embodiment of the first embodiment of the third aspect of the present invention, the hydrophobic organic solution furthermore comprises a fatty acid ester, preferably methyl laurate.

In a third embodiment of the fourth aspect, which is also an embodiment of the first to second embodiment of the second aspect of the present invention, the hydrophobic organic solution comprises oleic acid as cation exchanger and 25 to 75% by volume of methyl laurate as solvent.

In a fourth embodiment of the fourth aspect, which is also an embodiment of the first to third embodiment of the present invention, the organic compound is a compound according to one of the embodiments of the first aspect of the invention.

In a fifth aspect, the object of the present invention is achieved by a process for producing an organic compound with one or more positive charges, where the organic compound is toxic to cells, comprising culturing in an aqueous solution of cells involved in the synthesis of the organic compound, preferably cells which catalyze at least one step of the synthesis, in the presence of a hydrophobic organic solution comprising a liquid cation exchanger and optionally an organic solvent.

In a first embodiment of the fifth aspect of the present invention, the organic compound is 12-aminolauric acid or methyl 12-aminolaurate, and the organic solvent is methyl laurate.

The inventors of the present invention have found that the efficiency of removing an organic compound having one or more positive charges from an aqueous solution to a hydrophobic organic solution can surprisingly be increased if this organic solution comprises a liquid cation exchanger. Without wishing to be bound to any one theory, the inventors of the present invention assume that the negative charge or the negative charges of the liquid cation exchanger interacts/interact ionically with the one or more positive charges of the organic compounds and that this interaction leads to a masking of at least one positive charge, which increases the solubility in the organic phase.

In a preferred embodiment, the term "liquid cation exchanger", as used herein, means a compound that is soluble in a hydrophobic organic solvent and which, on account of one or more negative permanent charges, is able to form an ionic interaction with at least one cation. Typically, a liquid cation exchanger comprises at least one saturated or unsaturated hydrocarbon chain, which may be straight-chain or branched, and also a negatively charged group, for example a carboxy group. In one preferred embodiment, the liquid ion exchanger is a fatty acid, in a further preferred embodiment an unsaturated fatty acid, for example oleic acid. In one preferred embodiment, the liquid ion exchanger is di(2-ethylhexly)phosphoric acid (also referred to as DEHPA or D2EHPA).

In a preferred embodiment, the liquid ion exchanger has not only an overall negative charge, but no positive charge at all. In a third embodiment, the term "overall charge" of the ion exchanger or of any other molecule, as used herein, is understood as meaning the sum of the charges of all functional groups bonded covalently to the molecule. For example, lauric acid has a negative charge as overall charge, irrespective of the presence of further molecules or counterions which are present in the aqueous solution.

In a preferred embodiment of the present invention, the term "contacting", as used herein, is understood as meaning that two phases are exposed to one another directly and especially without interposition of a physical barrier such as a membrane. Contacting takes place in the simplest case by placing the two phases into the same vessel and mixing them together in a suitable manner, for example by stirring.

In one preferred embodiment, the organic compound has an overall positive charge. In a further preferred embodiment, the organic compound does not have negative charges. In one preferred embodiment, the organic compound is an w-aminocarboxylic acid. In one preferred embodiment, the wording "one or more" charges of a certain type means at least one corresponding charge.

In a preferred embodiment, the term "has a charge", as used herein, means that a compound referred to in this way has a corresponding charge in aqueous solution at pH 0 to 14, preferably 2 to 12, 2 to 6, 8 to 12, 3 to 10, 6 to 8, most preferably at pH 7. In a preferred embodiment, it is a permanently present charge. In a further preferred embodiment, the term "has a charge", as used herein, means that the corresponding functional group or compound is present at pH 7 predominantly with the corresponding charge, i.e. to at least 50, more preferably 90, even more preferably 99%. In a further preferred embodiment, an amino group ($-NH_2$) counts in a molecule as a group with a positive charge, irrespective of whether it is present in complete protonated form, partially protonated form or completely unprotonated form.

In one preferred embodiment of the invention, the term "comprising" is to be understood in the sense of "including", i.e. not definitively. A mixture comprising A can in this sense have further constituents as well as A.

In a preferred embodiment, the term "hydrophobic", as used herein, is understood as meaning the property of the liquid, in the presence of an aqueous phase, to form its own liquid phase that is clearly defined from the aqueous phase. The latter may be a continuous liquid phase or an emulsion. In a further preferred embodiment, the term "hydrophobic", as used herein, is understood as meaning the property of a compound to essentially not dissolve in water. Finally, the term in a further preferred embodiment, as used herein, is understood such that such a compound referred to in this way has a P value (J. Sangster, *Octanol-Water Partition Coefficients: Fundamentals and Physical Chemistry*, Vol. 2 of *Wiley Series in Solution Chemistry*, John Wiley & Sons, Chichester, 1997) whose logarithm in base 10 is greater than 0, more preferably greater than 0.5, even more preferably greater than 1 and most preferably greater than 2.

In a further embodiment of the present invention, the liquid ion exchanger has no or only a moderate toxic effect on biotechnologically relevant microorganisms. The term "toxic effect", as used herein, is understood, in a preferred embodiment of the invention, as meaning the property of a compound, upon contact with the corresponding microorganisms, to reduce their growth rate, to reduce their metabolic activity, to increase their energy consumption, to reduce their optical density or number of cells capable of growth and/or to lead directly to their death and lysis. In a preferred embodiment, at least one of these effects is achieved for a toxic compound even at low concentration, preferably at a concentration of 1000, more preferably 100, even more preferably 50 or 25, most preferably 5 mg/L. The person skilled in the art is aware of numerous methods that can be used routinely to investigate toxicity. These include, for example, measuring the respiration of corresponding microorganisms via $O_2$ electrodes or the comparative plating out of microorganism samples and the subsequent counting of the colony-forming units (CFUs). In a preferred embodiment, a "moderate toxic effect" is understood as meaning that microorganisms in a growth phase in the presence of the compound grow further and/or are metabolically active, but to a lesser extent than in the case of a control which is incubated under identical conditions in the absence of the corresponding compound, and/or have an extended lag phase.

The contacting of aqueous and organic solution takes place under suitable conditions and in particular over a period which suffices for an adequate transfer of the organic compound from the aqueous phase to the organic phase, ideally even for establishing the corresponding equilibrium. This period of time conditions can be determined by the person skilled in the art in the course of routine experimentation.

In a particularly preferred embodiment, the organic compound having one or more positive charges is a terminally aminated fatty acid, particularly preferably 12-aminolauric acid or an ester thereof or a mixture of both compounds. The person skilled in the art will recognise that an ester of a fatty acid, in the presence of a biological system comprising esterase activities, can be present partially in the form of the corresponding acid and both compounds should in this connection be considered in this regard to be equivalent.

Accordingly, fatty acids or fatty acid derivatives in a particularly preferred embodiment, as used herein, also include the corresponding esters, preferably methyl esters, and vice versa.

In a particularly preferred embodiment, the term "alkylene group", as used herein, is a group of the Formula —$(CH_2)_n$—, i.e. an alkane with two left-open, preferably terminal substituents. The two substituents may be e.g an amino group and a carboxy group. In a preferred embodiment, n is at least 3, more preferably at least 6, more preferably 11. In a "substituted alkylene chain", at least one hydrogen atom is replaced by a substituent other than a hydrogen atom or an alkyl radical, preferably an atom other than a hydrogen atom. In one particular embodiment, the term "unsubstituted alkylene group", as used herein, by contrast means a hydrocarbon chain of the Formula —$(CH_2)_n$— without a substituent of this type.

In a particularly preferred embodiment of the present compound, the organic compound with one or more positive charges is a cyclic sugar. In a further particularly preferred embodiment, this cyclic sugar has at least two amino groups. In an even more preferred embodiment, the "cyclic sugar" is a sugar selected from the diaminodianhydrodideoxyhexitols, particularly 2,5-diamino-1,4:3,6-dianhydro-2,5-dideoxy-D-hexitol, in a most preferred embodiment the three stereoisomers thereof, 2,5-diamino-1,4:3,6-dianhydro-2,5-dideoxy-D-mannitol (I), 2,5-diamino-1,4:3,6-dianhydro-2,5-dideoxy-D-glucitol (II) and 2,5-diamino-5 1,4:3,6-dianhydro-2,5-dideoxy-L-iditol (III), which differ in the chirality at position 2 and 5. The amino groups can here be in the endo, endo (I), endo, exo (II) or exo, exo (III) position, based on the chair form of the fused five-membered rings.

In a preferred embodiment of the present compound, in combination with a cyclic sugar as organic compound to be removed, a compound is used as solvent which is selected from the group which is selected from the group which comprises kerosene (K), benzyl benzoate (B), methyl laurate (ML), cis-9-octadecen-1-ol (OD).

In a particularly preferred embodiment, the organic compound is DAI (diaminoisoiditol) or DAS (diaminoisosorbitol), the liquid cation exchanger is an unsaturated fatty acid, preferably oleic acid, and the aqueous phase has a pH of at least 6.5 or 7, preferably 7 to 10, more preferably 7.5 to 9.5.

In a particularly preferred embodiment, the organic compound is DAI or DAS, the liquid cation exchanger is DEHPA, and the aqueous phase has a pH of at least 3 or at least 3.5, preferably 3 to 8, preferably 4 to 10, more preferably 4.5 to 9, more preferably 4.5 to 7 or 5 to 8.

In a preferred embodiment, the mixture that is formed by contacting aqueous and hydrophobic phase is exposed to an elevated temperature for the purpose of better phase separation as part of step c) or in an additional step in order to promote phase separation. For example, temperature can be increased under standard pressure to above 50, 55, 60, 65, 70, 75, 80, 85, 90 or 95° C.

The temperature in step b) depends not only on the properties of the liquid cation exchanger, but, particularly if the contacting of the aqueous and the organic solution takes place as the reaction proceeds in the aqueous phase, also on the temperature requirements of any reactions that are taking place in the aqueous phase. Particularly if a biological agent such as a living cell is catalytically active in the aqueous phase, the temperature must be suitable for retaining this activity. In a preferred embodiment, the temperature in step b) is 0 to 100° C., more preferably 20 to 80° C., 28 to 70° C., 30 to 37° C., 35 to 40° C.

The pH in step b) must also take into consideration the requirements of any simultaneously proceeding reactions, the stability of starting materials, products, intermediates or agents. In a preferred embodiment, the pH is 3 to 8, more preferably 6 to 8, even more preferably 6.2 to 7.2.

In order to transfer the organic compound from the aqueous phase as completely as possible to the organic phase, a sufficient amount of the liquid cation exchanger is required. In a preferred embodiment of the present invention, the quantitative ratio of liquid cation exchanger and organic compound in at least one step, in a continuous process summed over the entire course of the reaction, is at least 1, i.e. at least one molecule of liquid cation exchanger is used per molecule of the organic compound. In an even more preferred embodiment, the ratio is greater than 2, 3, 5, 10, 15, or 20, preferably 1.5 to 3.

In a preferred embodiment, whether the cation exchanger is a liquid cation exchanger is determined by its state of aggregation at the processing temperature, preferably at 37° C. If the cation exchanger is used in an organic phase which has further compounds alongside the cation exchanger, then the state of aggregation of the mixture is decisive. It suffices if—optionally using routine processes known from the prior art—a mixture can be prepared which is liquid overall at the processing temperature, preferably at 37° C., and comprises the liquid cation exchanger. For example, it may be necessary to dissolve the cation exchanger at a higher temperature than that used in the process and to cool the mixture to processing temperature.

The volume ratio of the organic solution to the aqueous solution is, together with the cation exchanger/organic compound quantitative ratio, significant for an efficient process. In one particular embodiment, it is 100:1 to 1:100, more preferably 20:1 to 1:20, even more preferably 10:1 to 1:10, 4:1 to 1:4, 3:1 to 1:3 or most preferably 1:2 to 2:1.

In a preferred embodiment of the present invention, a fatty acid is used as liquid cation exchanger. In a preferred embodiment of the present invention, the term "fatty acid", as used herein, is understood as meaning a carboxylic acid, preferably alkanoic acid, having at least 6, preferably 8, more preferably 10, most preferably 12, carbon atoms. In a preferred embodiment, they are straight-chain fatty acids and in a further embodiment branched ones. In one preferred embodiment, they are saturated fatty acids. In a particularly preferred embodiment, they are unsaturated ones. In a further preferred embodiment, it is a straight-chain fatty acid with at least 12 carbon atoms containing a double bond, preferably at position 9. In a further preferred embodiment, it is a monounsaturated fatty acid in which the double bond is at position 9 and/or 11. In a further preferred embodiment, the liquid cation exchanger is an unsaturated fatty acid selected from the group comprising oleic acid, palmitoleic acid and gadoleic acid and icosenoic acid. In the most preferred embodiment, it is oleic acid. In a particularly preferred embodiment, it is a fatty acid having 6, 7, 8, 9, 10, 11, 12, 13, 14, 15, 16, 17, 18, 19, 20, 21, 22, 23, 24, 25, 26, 27, 28, 29, 30 carbon atoms, preferably more than 12, yet more preferably more than 14, carbon atoms, yet more preferably having 14 to 28, 14 to 22, most preferably 16 to 18, carbon atoms.

In a further preferred embodiment, the liquid ion exchanger used is a mixture of different fatty acids, as is present for example in the form of soya oil or globe thistle oil. In this case, the fatty acids have to be released under certain circumstances by hydrolysis of the corresponding ester, which can be accomplished by reducing the pH or similar measures known as routine procedure to the person skilled in the art.

In a particularly preferred embodiment of the present invention, a combination of two liquid cation exchangers, preferably at least one of them a fatty acid, is used.

A particular advantage of the present invention lies in the compatibility of the process according to the invention with biotechnological processes and biological agents used therein. In one particular embodiment of the present invention, the term "biological agent with catalytic activity", as used herein, is understood as meaning a biocatalyst synthesized by a cell in all stages of purification, from the entire cell to the isolated molecule. In a preferred embodiment, it is a cell expressing enzymes with catalytic activity. The cell may be a prokaryotic, including Archaea, or a eukaryotic, preferably from the group comprising *Pseudomonas, Corynebacterium* and *E. coli*. In a yet more preferred embodiment, the agent is a bacterial cell, more preferably a gram-negative bacterial cell, most preferably *E. coli*. In a further preferred embodiment, it is a eukaryotic cell, more preferably a fungus cell, yet more preferably a yeast cell, most preferably *Saccharomyces* or *Candida, Pichia*, in particular *Candida tropicalis*. The term "cell" is, in a particular embodiment, used in this applications synonymously and exchangeably with the term "microorganism". Furthermore, the cell may be an isolated cell or a mixture of cultures.

The cell used as biological agent can be viable, or it may be a preparation thereof, for example a membrane fraction or cytosolic fraction or a crude extract of the cell.

If the biological agent is an isolated molecule in various stages of purification, then this can be all catalytically active molecules produced by a cell. In a particularly preferred embodiment, it is a molecule from the group comprising peptides, polypeptides, carbohydrates, nucleic acids or mixed forms thereof. In an even more preferred embodiment, it is a catalytically effective polypeptide. In a further preferred embodiment, it is an immobilized molecule.

The catalytic functions required for synthetic biotechnological processes are diverse. In a preferred embodiment, the term "catalytic activity" as used herein, is a synthetic activity, i.e. the catalysis of chemical reactions involving the formation of at least one new covalent bond. In a further preferred embodiment, it is a transport activity, i.e. the ability of a molecule to effect transportation of another molecule from one compartment to another, e.g. the absorption of a substance from the aqueous medium via a cell membrane into the interior of the cell.

In a particularly preferred embodiment, the biological agent is a living cell which is used in the presence of the liquid cation exchanger for the catalysis, preferably in order to synthesize an organic compound with one or more positive charges, which is removed subsequently or simultaneously by means of the liquid cation exchanger to a hydrophobic organic phase.

In a particularly preferred embodiment, the presence of the organic compound has a disadvantageous effect on the catalytic activity. In one embodiment, this can reduce the amount of available activity, which can be expressed in the sense of a lower $k_{cat}$ of an enzyme. In a further embodiment, the affinity of the agent having the catalytic activity can be effected in the sense of an increased $K_M$ of an enzyme. In a further embodiment, the specificity of the catalytic activity can be altered, for example in such a way that it preferentially converts, or preferably converts, a substrate molecule other than the desired substrate molecule. In a further embodiment, the organic compound has a toxic effect on a cell as biological agent.

In a further embodiment, the organic compound is an organic compound which reduces the availability of an essential co-substrate or co-enzyme. This can e.g. be the case if the organic compound inhibits a corresponding regeneration reaction.

Besides the liquid cation exchanger, the hydrophobic organic phase can furthermore comprise a hydrophobic solvent. This can serve to increase the absorption capacity of a liquid cation exchanger in the hydrophobic phase and to prevent undesired behaviour, for example flocculation. In a preferred embodiment, the solvent is a starting material of a reaction proceeding in the aqueous solution, most preferably the substrate of an enzyme-catalyzed reaction proceeding in the aqueous solution. In a preferred embodiment, it is a fatty acid ester. In a particularly preferred embodiment, the solvent is a fatty acid ester, preferably methyl ester, of a fatty acid which serves as liquid cation exchanger.

The fraction of the solvent, if present, in the hydrophobic organic phase is, in one preferred embodiment, 1 to 99 percent by volume (% by volume). In a preferred embodiment, the fraction of the solvent is 10 to 90, more preferably 20 to 80, most preferably 25 to 75% by volume.

In a most preferred embodiment of the process, the organic compound is 12-aminolauric acid and/or methyl 12-aminolaurate, which is prepared in the aqueous phase by a recombinant *E. coli* strain by stepwise oxidation of the terminal carbon atom of methyl laurate, as disclosed in DE10200710060705, and the hydrophobic phase comprises 25 to 75% oleic acid as liquid cation exchanger dissolved in methyl laurate as substrate of the reaction.

In a preferred embodiment, the organic compound is a compound of the Formula $H_2N$—$(CH_2)_x$—$NH_2$. Here, x can assume the values 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, preferably 1 to 20, even more preferably 1 to 10.

The present invention is furthermore illustrated by the following figures and limiting examples, which reveal further features, embodiments, aspects and advantages of the present invention.

EXAMPLE 1

Figure 1:
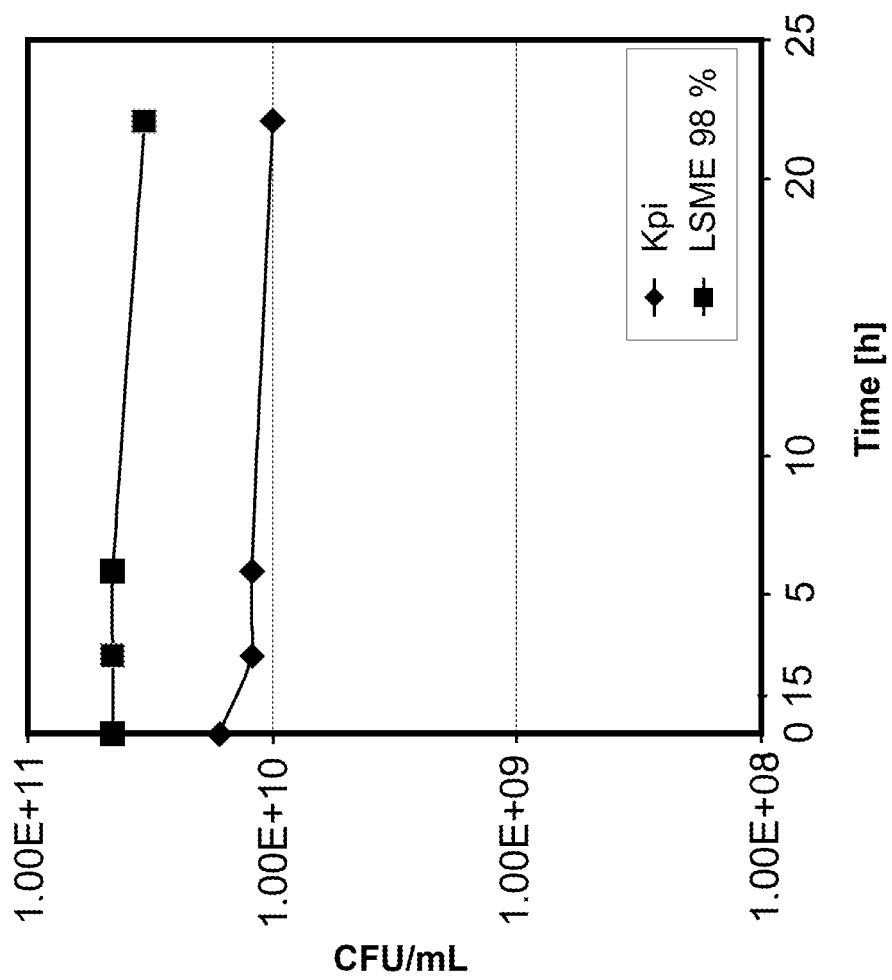
FIG. 1 shows a control experiment for confirming that LSME does not have a toxic effect, investigated with a *E. coli* W3110 strain and compared to potassium phosphate buffer (Kpi) as negative control.

Investigation of the Toxicity of the Solvent LSME which is Used in Compositions with Liquid Cation Exchanger This experiment was used to show the relatively low toxicity of LSME with regard to biotechnologically relevant microorganisms, which makes LSME a suitable organic solvent for the process according to the invention.

Before the determination of the CFU was able to be carried out, a plate LB (10 g/L peptone from casein, 5 g/L yeast extract, 10 g/L NaCl) was streaked with *E. coli* BW3110 and incubated for 24 h. On the evening of the following day, a preculture was inoculated from this previously streaked plate. This preculture had a volume of 50 mL LB medium and was incubated overnight for ca. 16 h. On the following day, the preculture with an $OD_{600}$ of 0.2 in 200 mL of M9 medium (Na2HPO4 6.79 g/L; KH2PO4 3.0 g/L; NaCl 0.5 g/L; NH4Cl 1 g/L; 1 mL/L trace element solution, pH 7.4. Trace element solution: HCl 37% (=455.8 g/L) 36.50 g/L; MnCl2*7H2O 1.91 g/L; ZnSO4*7H2O 1.87 g/L; Na EDTA*2H2O (Titriplex III) 0.84 g/L; H3BO3 0.30 g/L; Na2MoO4*2H2O 0.25 g/L; CaCl2*2H2O 4.70 g/L; FeSO4*7H2O 17.80 g/L; CuCl2*2H2O 0.15 g/L) was transinoculated with 3% glucose (w/v) and incubated for ca. 20 h. After the incubation of the main culture, the cells were harvested, centrifuged at 5258 g and 4° C. for 10 min and resuspended with an $OD_{600}$ of 30 in 10 mL 50 mM Kp, buffer at pH 7.4 (or 25 mM HEPES buffer pH 7.4 if CFU determinations were carried out with ALSME). Both buffer solutions used contained 5% glucose (w/v). The bacteria suspension was then transferred to the shake flasks and treated with the respective substance solutions. After thorough mixing has taken place by swirling the flask, 100 µL of the suspension was pipetted out and placed into 900 µL, of previously charged sterile saline. This corresponded to sampling at time point $t_0$. Then followed incubation of the preparations at 250 rpm and 30° C. The CFUs were determined over a period of 22 h. The samples were taken firstly at time points $t_0$, $t_3$, $t_6$ and $t_{22}$. For some preparations, a further sampling time point $t_{15}$ was added and, in addition to this, a further additional dilution series was plated out in order to minimize deviations.

The $OD_{600}$ was 60. The cells were resuspended in 10 mL of Kp, buffer and then mixed in the flask with 5 mL of LSME 98% (w/w). One dilution stage per preparation was plated out. The number of CFU/mL remained constant over a period of 6 h. After 22 h, a percentage decrease in living cell count of just 30.3% was recorded.

EXAMPLE 2

Comparative Experiments Relating to the Toxicity of Various Liquid Cation Exchanger Towards Biotechnologically Relevant Microorganisms This example shows the lower toxicity of unbranched fatty acids compared with other liquid cation exchangers such as DEHPA as well as branched and unbranched saturated fatty acids.

Firstly, a preculture comprising 20 ml LB medium was inoculated in a 100 ml baffled flask with a cryoculture of the corresponding strain. The culture was cultured overnight at 37° C. and with shaking at 200 rpm used on the next day in order to inoculate an identical main culture to an OD of 0.2. The main cultures (each 30 mL of LB medium) were then further incubated under identical conditions. At an OD of 0.4 to 0.5, the main culture was covered with in each case identical volumes (30 ml) of solvent and then further incubated.

To determine the number of CFU (colony-forming units) 0.1 ml samples were taken in the following experiments and diluted in sterile 0.9% NaCl solution. Suitable dilution stages were plated out on LB agar plates. After incubation at 34° C. overnight, the colonies formed were counted and the CFUs determined.

Experiment 1: Comparison of the Toxicity Between DE2HPA and a Saturated Fatty Acid as Liquid Cation Exchanger 50% DEHPA and lauric acid (15%), each dissolved in LSME and laden equimolar or 25 mol % with ALSME, were contacted as liquid cation exchanger with a *E. coli* BL21 (DE3) strain, and the influence of these two compounds on the ability of the strain to form colonies, expressed in CFUs, was investigated. Preliminary experiments showed that methyl laurate—which could not function as a liquid cation exchanger on account of a lack of charge—is well tolerated by the strains used.

TABLE 1

| Experiment No. | *E. coli* strain used | Liquid cation exchanger used | Number of CFUs after 22 or 24 h relative to t = 0 h |
|---|---|---|---|
| 1a | *E. coli* BL21(DE3) | None | 244% |
| 1b | *E. coli* BL21(DE3) | DEHPA | 0% |
| 1c | *E. coli* BL21(DE3) | Lauric acid | 1.2% |

It is found that both liquid cation exchangers significantly reduce the number of CFUs, but when using lauric acid in contrast to DEHPA still a few viable cells are present and the saturated fatty acid is therefore to be preferred as liquid cation exchanger.

Experiment 2: Comparison of the Toxicity Between Branched Saturated Fatty Acids and Various Amounts of Oleic Acid as Liquid Cation Exchanger For this, two different concentrations of oleic acid were used and the volume was adapted by adding the corresponding amount of LSME (methyl laurate).

TABLE 2

| Experiment No. | *E. coli* strain used | Liquid cation exchanger used | Number of CFUs after 22 or 24 h relative to t = 0 h |
|---|---|---|---|
| 2a | *E. coli* BL21(DE3) | Isononanoic acid | 0 |
| 2b | *E. coli* BL21(DE3) | 2-Ethylhexanoic acid | 0 |
| 2c | *E. coli* BL21(DE3) | LSME/25% oleic acid | 11% |
| 2d | *E. coli* BL21(DE3) | LSME/75% oleic acid | 18% |
| 2e | *E. coli* W3110 | Isononanoic acid | 0 |
| 2f | *E. coli* W3110 | 2-Ethylhexanoic acid | 0 |
| 2g | *E. coli* W3110 | LSME/25% oleic acid | 29% |
| 2h | *E. coli* W3110 | LSME/75% oleic acid | 17% |

It is found that the number of viable cells when using the unsaturated fatty acid oleic acid together with LSME is consistently significantly higher than when using branched saturated fatty acids.

Experiment 3: Comparison of the Toxicity Between Unbranched Saturated Fatty Acids and Unsaturated Fatty Acids as Liquid Cation Exchanger Here, different amounts of an unsaturated fatty acid were compared with an unsaturated fatty acid as regards their toxicity when being used as liquid cation exchanger compared. On account of the lower solubility of the unsaturated fatty acid lauric acid, this was used in a smaller amount. The volumes of the different cation exchangers were made the same with the LSME. The number of CFUs was determined at the start, after 4.5 h and after 24 h.

Figure 2:
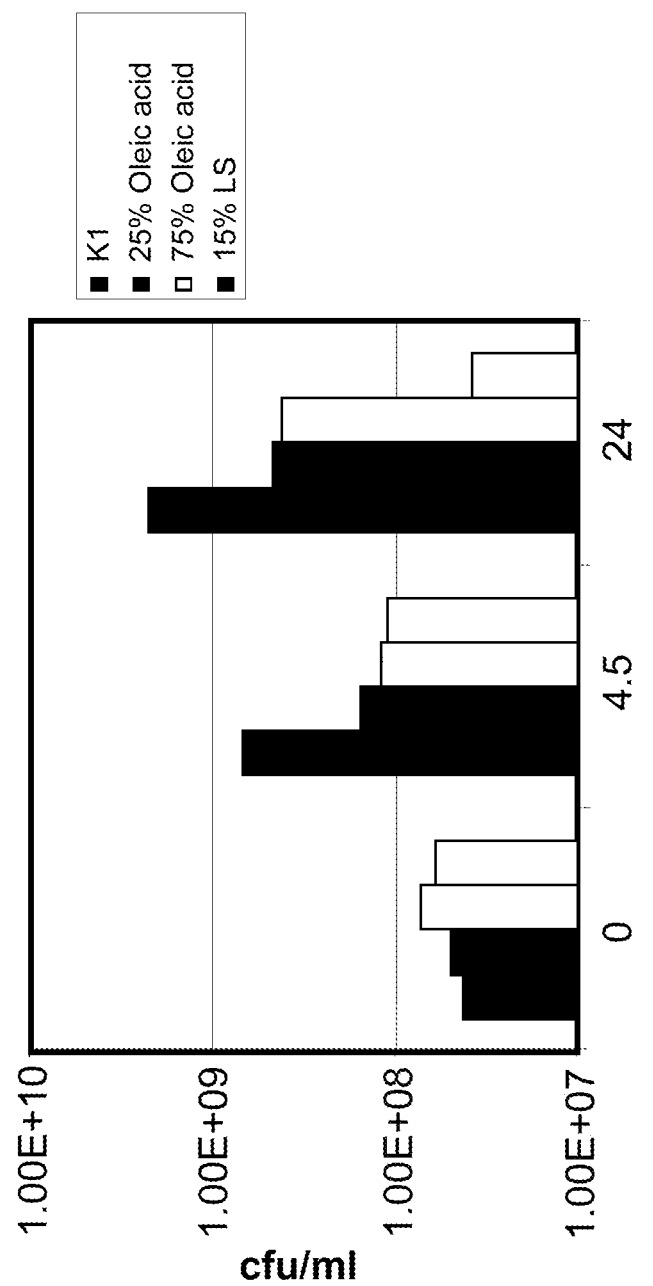
FIG. 2 shows the viability of the strain *E. coli* W3110 in the form of the number of CFUs which the strain can form in the absence of a liquid cation exchanger and in the presence of different liquid cation exchangers after 0 h, 4 h and 24 h.

As FIG. 2 reveals, the addition of the saturated fatty acid as liquid cation exchanger, even at a lower concentration than that of the unsaturated fatty acid, brings about a decrease in the CFUs, whereas in the case of the unsaturated fatty acid an increase in the CFUs is established.

Overall, a decrease in the toxicity for the various investigated liquid cation exchangers in the following order is found: DEHPA>saturated fatty acids>unsaturated fatty acids.

EXAMPLE 3

Removal of Diaminoisoiditol (DAD and Diaminoisosorbitol (DAS) Using Various Liquid Cation Exchangers from an Aqueous Phase This example shows that a liquid ion exchanger, here D2EHPA or oleic acid, as constituents of an organic hydrophobic phase increases the absorption capacity of the hydrophobic phase for a positively charged compound.

The organic solvents used here are kerosene (K), benzyl benzoate (B), methyl laurate (ML), cis-9-ocitadecen-1-ol (OD). As liquid cation exchangers, oleic acid and D2EHPA were compared in terms of their effect with the respective pure solvent.

The experimental procedure proceeded identically in all cases: the aqueous phase comprised 2% by weight of diamine and the organic phase consisted of the corresponding solvent and 20% by weight of the respective liquid cation exchanger. The volume ratio of the two phases was 1:1 (in each case 4.5 ml). At a constant temperature of T=30° C., the samples were shaken for 2 hours in a water bath. Then, after centrifugation and phase separation, the phases were analyzed. The pH was adjusted in all cases with aqueous ammonia or sulphuric acid.

Figure 3A:
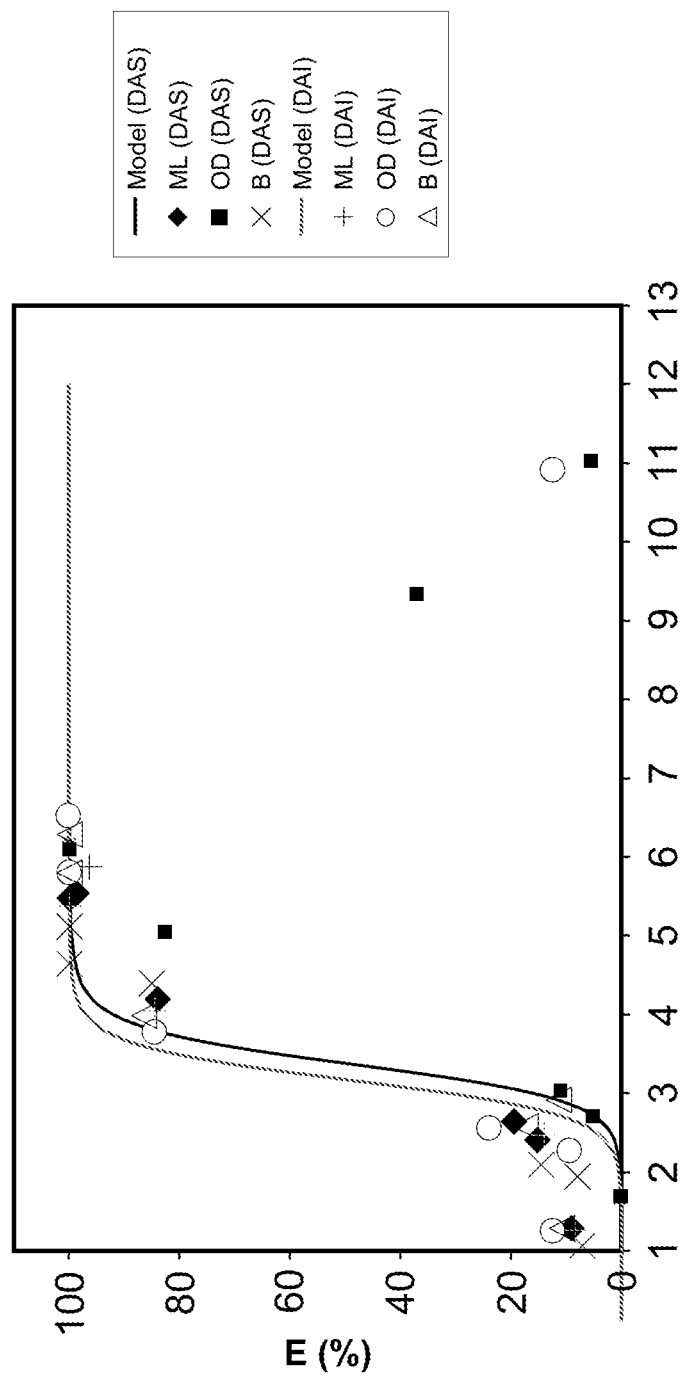
FIG. 3a shows the results of removing diaminoisoiditol (DAI) and diaminoisosorbitol (DAS) from an aqueous phase using D2EHPA as liquid cation exchanger.

FIG. 3a shows the results of the reactive extraction with D2EHPA as liquid cation exchanger. Without the addition of acid or alkali, the degree of extraction in the case of a pH range from 5.4 to 6.2 is ca. 100%. The addition of acid leads to a considerable reduction in the degree of extraction. In the event of adding a small amount of alkali, no influence on the degree of extraction is evident for the experiments with benzyl benzoate. If a large amount of alkali was added, starting pH from 11 to 12, the experiments could not be evaluated. When using DAS with cis-9-octadecen-1-ol as solvent, a reduction in the degree of extraction with increasing pH is observed, although the samples were milky/cloudy, in the event of the extraction of DAI, upon the addition of a small amount of alkali no significant influence on the degree of extraction is evident, in the case of an initial pH of 11 to 12 the degree of extraction drops significantly, the two phases remaining milky/cloudy despite repeated centrifugation, a ca. 1.5 cm thick white layer was evident at the phase boundary. When methyl laurate was used as solvent, the addition of a small amount of alkali, initial pH 10 to 11, led to a slight drop in the pH, and the phase was milky/cloudy. The addition of a large amount of alkali led to the formation of a single clear phase.

Figure 3B:
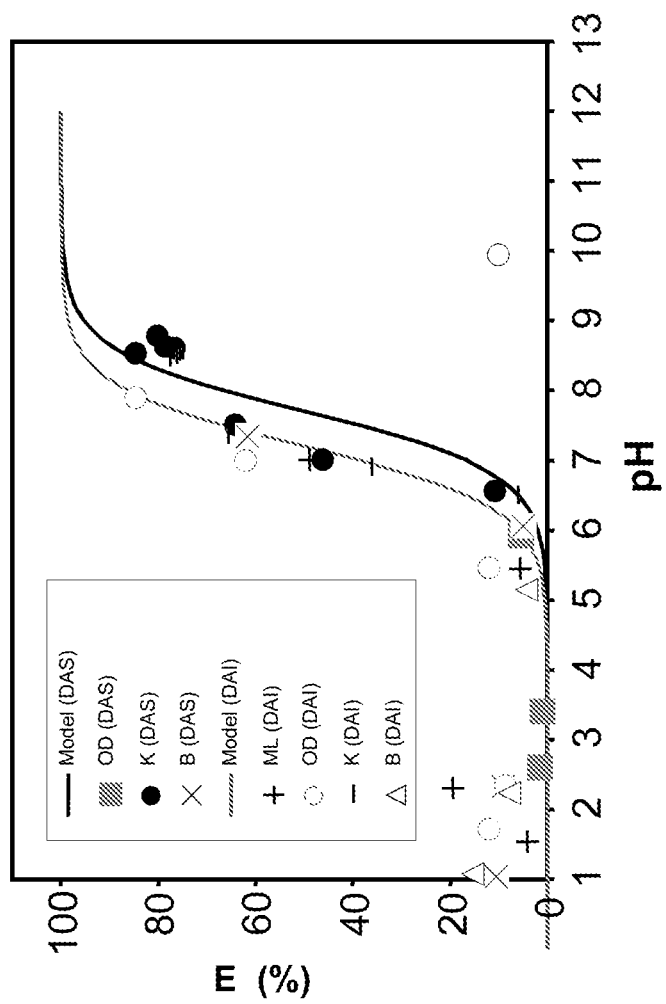
FIG. 3b shows the results of removing DAI and DAS from an aqueous phase using oleic acid as liquid cation exchanger.

The results of using oleic acid as liquid cation exchanger are shown in FIG. 3b. In the course of the experiments, a degree of extraction of 100% was not achieved. The experiments with methyl laurate as solvent could only be evaluated if sulphuric acid was used during the preparation to lower the pH. The maximum degree of extraction achieved was 4% in the case of the extraction of DAS and 48% in the case of that of DAI. The experiments as regards the extraction of DAS with cis-9-octadecen-1-ol as solvent could likewise only be evaluated if the starting pH was reduced with H2SO4. A maximum degree of extraction of 5.5% at pH 6 was achieved. In the case of the extraction of DAI, a maximum degree of extraction of 85% was achieved at pH 7.9 if neither alkali nor acid was added. The addition of alkali led to a significant decrease in the degree of extraction. When using kerosene as solvent for the extraction of DAS, a maximum degree of extraction of 85% at PH 8.5 and, in the case of the extraction of DAI, a maximum degree of extraction of 77.5% at pH 8.4 are achieved. The addition of alkali leads to a very slight reduction in the degree of extraction. The experiments with benzyl benzoate could be evaluated only in cases where the pH of the aqueous phase had been lowered with sulphuric acid before the start of the experiment. The maximum degree of extraction in the case of the extraction of DAS is 61.5% at pH 7.3, that of DAI 15.3 at pH 1.1. Above pH 6, a further lowering leads to an increase in the degree of extraction. The aqueous phase remained cloudy even after centrifugation for 45 minutes.

Figure 3C:
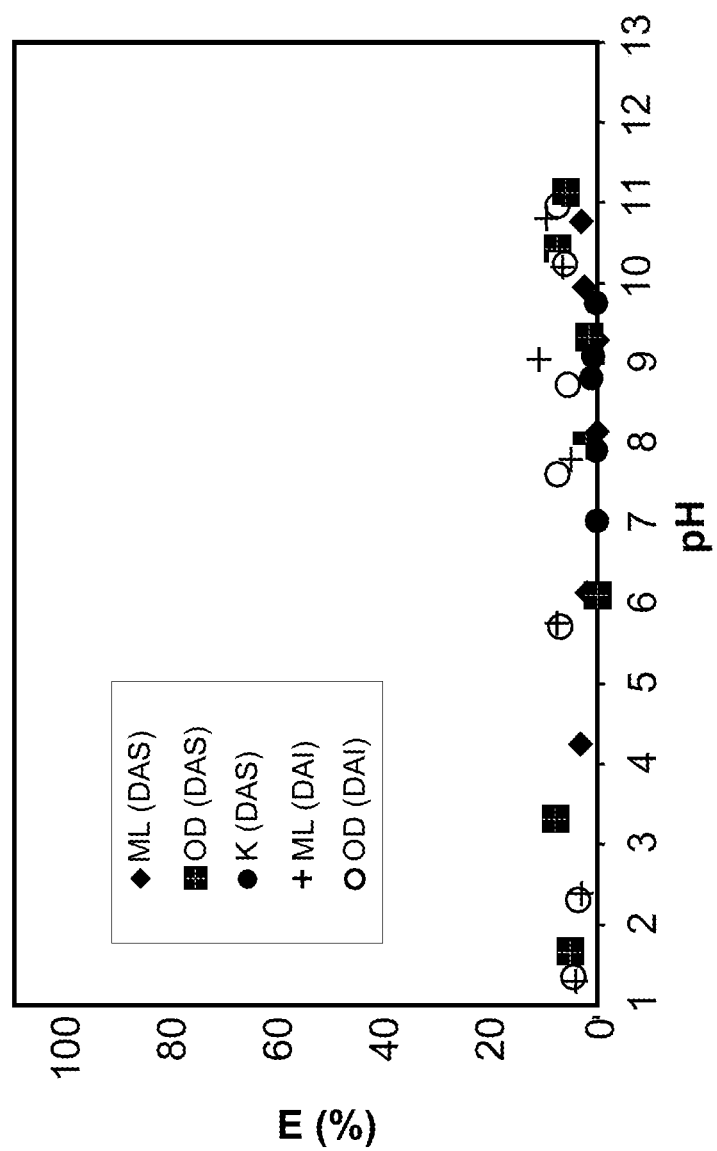
FIG. 3c shows the results of removing DAI and DAS from an aqueous phase without using a liquid cation exchanger.

The degrees of extraction obtained in the corresponding comparative experiments with the same solvents but without liquid cation exchanger are shown in FIG. 3c, plotted against the pH. No clear dependency of the degree of extraction on the pH is evident. In every case, the degrees of extraction are significantly below 20%.

EXAMPLE 4

Reduction in the Toxicity of an Organic Compound with Positive Charge by Contacting with a Liquid Cation Exchanger This experiment shows that through the presence of a liquid cation exchanger the toxic effect of a positively charged organic compound in an aqueous phase which is a fermentation liquor can be reduced by extracting this compound into the organic phase.

The fundamental experimental procedure corresponded to that in Example 1.

Since ALSME 0.2% (w/v), dissolved in aqueous systems, had a bactericidal effect, this experiment was carried out again in combination with D2EHPNH3/LSME 2/98% (w/w) in the shake flask, D2EHPNH3 here meaning D2EHPA laden quantitatively with ammonium. The use of the liquid ion exchanger improves the transfer of ALSME into the organic phase, as a result of which its concentration in the aqueous phase, in which the cells are also located, is reduced. In order to reduce a toxic effect caused by D2 EHPA, low concentrations of 2% (w/w) D2EHPNH3 were used.

The bacteria were firstly resuspended in 5 mL (corresponds to half of the buffer volume). A further 5 mL of buffer were optionally admixed with 0.4% (w/v) ALSME and then optionally vortexed with 5 mL of D2EHPNH3/LSME 2/98% (w/w) for 1 min at 3000 rpm. This solution was added to the initially charged bacteria suspension in the shake flask and mixed. The first sample was then taken.

Figure 4:
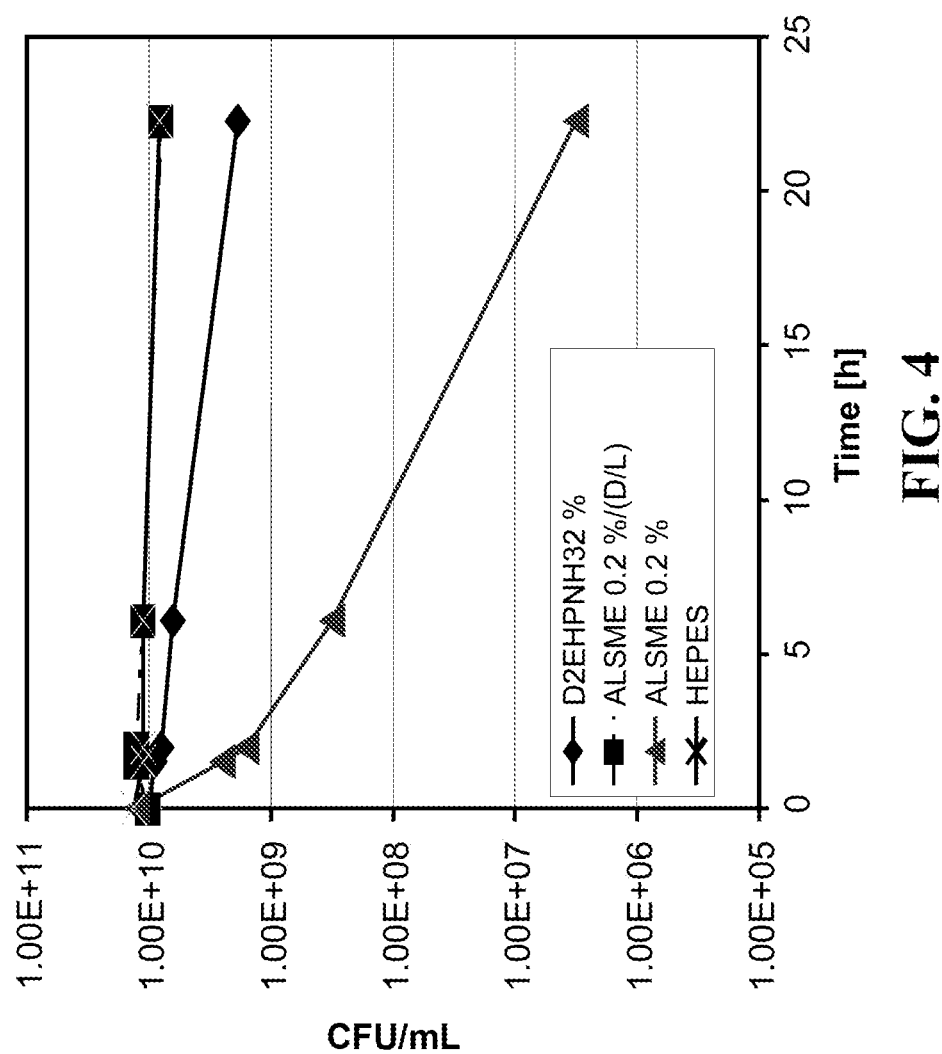
FIG. 4 shows the effect of using a liquid cation exchanger on the toxicity by reference to the change in living cell count of an *E. coli*—W3110 strain in the presence of ALSME 0.2%, with ammonia adjusted to DEHPA ("D2EHPNH3 2%") or a DEHPA/LSME mixture (2%/98%) ("D/L") in the presence of ALSME 0.2%.
Figure 5:
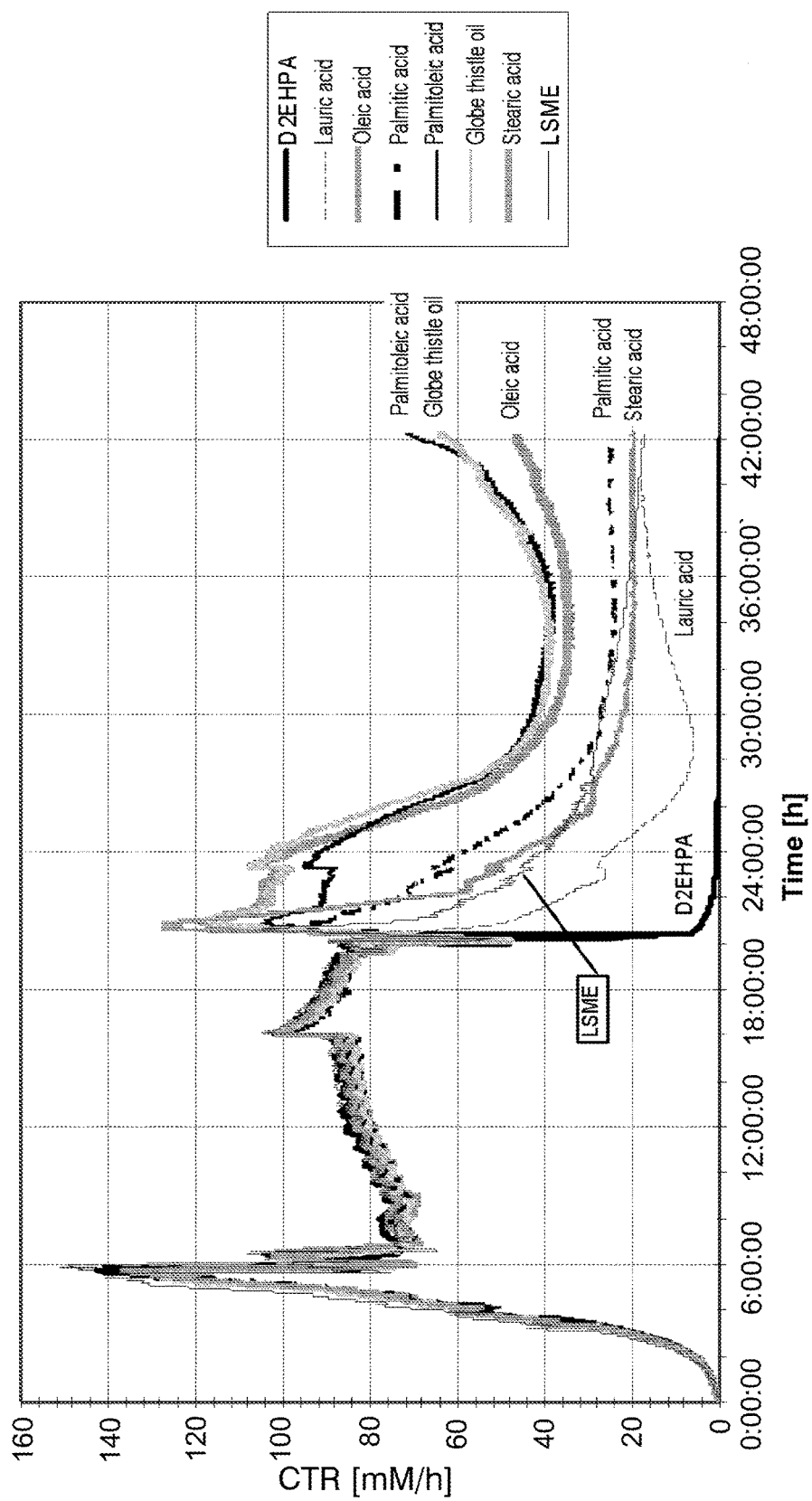
FIG. 5 shows the effect of different liquid cation exchangers on the OTR of methyl aminolaurate producing *E. coli* strain. The experiment was carried out as described in Example 5.
Figure 6:
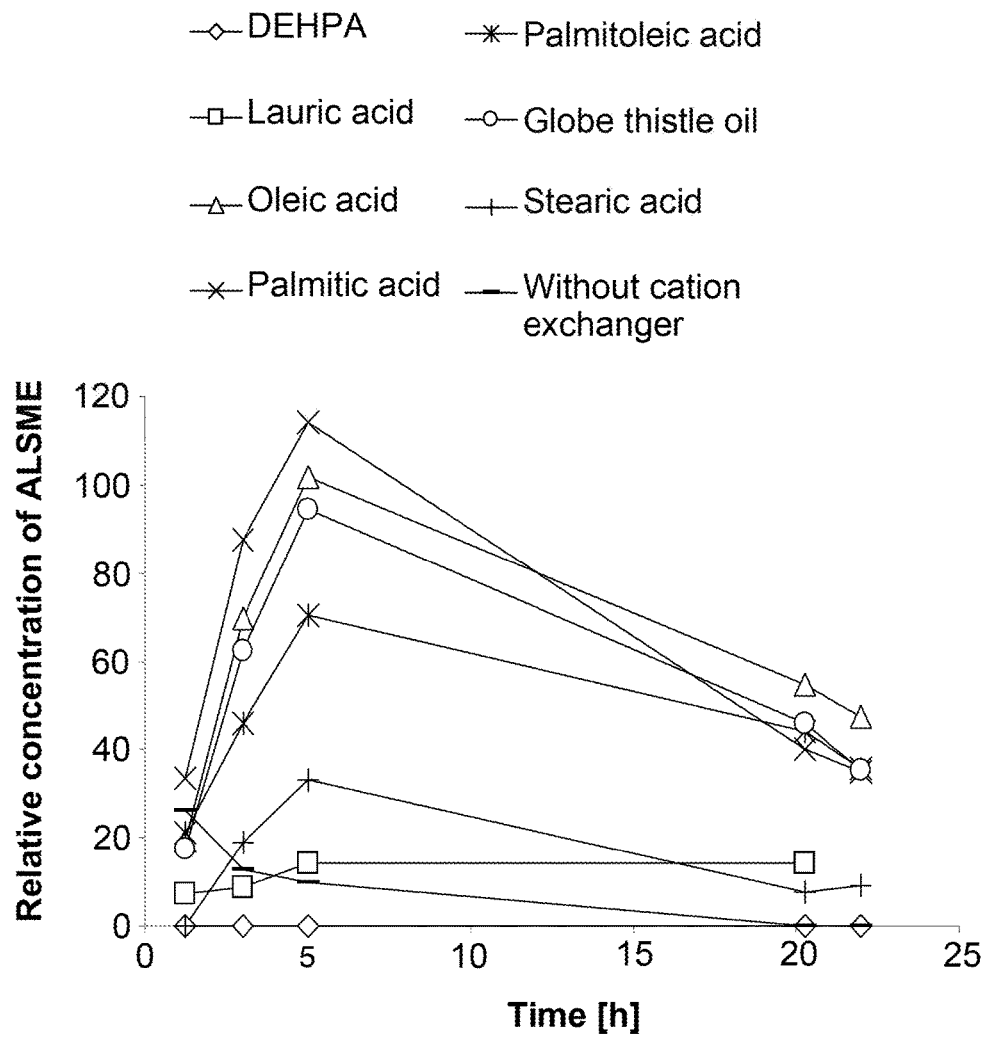
FIG. 6 shows the influence of different liquid cation exchangers on the yield of methyl aminolaurate which an *E. coli* strain with suitable genetic modification produces. The experiment was carried out as described in Example 5.

The solution had a foamy consistency at the start of the experiments, although this had disappeared in both experiments at the time of taking the second sample. The abbreviation "D/L" was used for D2EHPNH3 (D2EHPA laden with ammonia)/LSME 2/98% (w/w). Between the sampling $t_0$ and $t_{1.5}$ h the number of CFU/mL increased by 34.3%. From the sampling ($t_{1.5}$) to the last sampling ($t_{22}$) the number of CFU/mL reduced by 54.9%. Compared to the preparation with D2EHPNH3/LSME 2/98% (w/w) without the addition of ALSME 0.2% (w/v), the number of reproducible cells after 22 h was 4.5 times higher and, at 3.4%, not significantly lower than the average value of the control preparations in HEPES buffer (see FIG. 4). Compared to the preparation with ALSME 0.2% (w/v) in the shake flask, without the addition of an organic phase, the number of CFU/mL was 2800 times higher.

It is found that the presence of the liquid cation exchanger reduces the toxicity of the positively charged compound, determined here via the number of remaining CFUs.

EXAMPLE 5

Comparative Experiments Relating to the Toxicity of Various Liquid Cation Exchangers Towards a Microorganism Producing ω-Aminolauric Acid (ALS) and the Methyl Ester (ALSME)

The biotransformation of methyl laurate to methyl aminolaurate was tested in an 8-fold parallel fermentation system from DasGip with different ion exchangers.

1 L reactors were used for the fermentation. The pH probes were calibrated using a two-point calibration with measurement solutions of pH 4.0 and pH 7.0. The reactors were filled with 300 mL of water and autoclaved for 20 min at 121° C. in order to ensure sterility. The pO2 probes were then polarized overnight (at least 6 h). On the next morning, the water was removed under the clean bench and replaced by high cell density medium with 50 mg/L kanamycin and 34 mg/L chloramphenicol. Subsequently, the pO2 probes were calibrated with a one-point calibration (stirrer: 600 rpm/gassing: 10 sL/h air) and the feed, correctant and induction means stretches were cleaned by means of clean-in-place. For this, the tubes were flushed with 70% ethanol, then with 1 M NaOH, then with sterile demineralised water, and finally filled with the respective media.

The ALS and ALSME producing *E. coli* strain BL21 (DE3) Tlr pBT10 pACYC:Duet[TAcv] was firstly grown from cryoculture in LB medium (25 mL in a 100 mL baffled flask) with 50 mg/L kanamycin and 34 mg/L chloramphenicol overnight at 37° C. and 200 rpm for ca. 18 h. Then, 2 mL in each case were transinoculated in high cell density medium (glucose 15 g/L (30 mL/L of a separately autoclaved 500 g/L stock solution with 1% $MgSO_4*7H_2O$ and 2.2% $NH_4Cl$), $(NH_4)_2SO4$ 1.76 g/L, $K_2HPO_4$ 19.08 g/L, $KH_2PO_4$ 12.5 g/L, yeast extract 6.66 g/L, trisodiumcitrate dihydrate 11.2 g, ammonium iron citrate solution 17 mL/L of a separately autoclaved 1% strength stock solution, trace element solution 5 mL/L of separately autoclaved stock solution (HCl (37%) 36.50 g/L, $MnCl_2*4H_2O$ 1.91 g/L, $ZnSO_4*7H_2O$ 1.87 g/L, ethylenediaminetetraacetic acid dihydrate 0.84 g/L, $H_3BO_3$ 0.30 g/L, $Na_2MoO_4*2H_2O$ 0.25 g/L, $CaCl_2*2H_2O$ 4.70 g/L, $FeSO_4*7H_2O$ 17.80 g/L, $CuCl_2*2H_2O$ 0.15 g/L)) (3×25 mL in a 100 mL baffled flask) with 50 mg/L kanamycin and 34 mg/L chloramphenicol and incubated for a further 6 h at 37° C./200 rpm.

The 3 cultures were combined in a shake flask and the optical density was determined at 7.2. In order to inoculate the reactors with an optical density of 0.1, in each case 4.2 mL were drawn up in a 5 mL syringe and the reactors were inoculated by means of canulae via a septum.

The following standard program was used:

| | DO regulator | | | | pH regulator | | |
|---|---|---|---|---|---|---|---|
| Preset | 0% | | | Preset | | 0 ml/h | |
| P | 0.1 | | | P | | 5 | |
| Ti | 300 s | | | Ti | | 200 s | |
| Min | 0% | | | Min | | 0 mL/h | |
| Max | 100% | | | Max | | 40 mL/h | |

| N (Rotation) | From | To | XO2 (gas mixture) | From | To | F (gas flow) | From | To |
|---|---|---|---|---|---|---|---|---|
| Growth and biotransformation | 0% 400 rpm | 30% 1500 rpm | Growth and biotransformation | 0% 21% | 100% 21% | Growth and biotransformation | 15% 6 sL/h | 80% 72 sL/h |

| Script | |
|---|---|
| Trigger sharp | 31% DO (1/60 h) |
| Induction IPTG | 2 h after feed start |
| Feed trigger | 50% DO |
| Feed rate | 3 [mL/h] |

The experiment carried out can be divided into two phases, the cultivation during which the cells should reach a certain optical density, and the subsequent biotransformation during which the expression of the genes required for the biotechnological process for producing ALSME was induced. The pH values were regulated to pH 6.8 on the one hand with ammonia (12.5%). During cultivation and biotransformation, the dissolved oxygen (DO) in the culture was regulated at 30% via stirrer speed and gassing rate. The fermentation was carried out as a feed batch, where the feed start, 5 g/Lh glucose feed (500 g/L glucose with 1% MgSO$_4$*7H$_2$O and 2.2% NH$_4$Cl), was triggered via a DO peak. With feed start, the temperature was also reduced from 37° C. to 30° C. The expression of the transaminase was induced 2 h after feed start via the automatic addition of IPTG (1 mM). The induction of the alk-genes was carried out by the manual addition of DCPK (0.025% v/v) 10 h after feed start. Before the start of the biotransformation, the optical density of the culture broths was determined.

The start of the biotransformation phase was carried out 14 h after feed start. For this, 150 mL of a mixture of methyl laurate and the respective ion exchanger (10% w/w) were added as a batch to the fermentation broth. The ion exchangers used were di(2-ethylhexyl)phosphoric acid (DEHPA), lauric acid, oleic acid, palmitic acid, palmitoleic acid, stearic acid and a mixture of free fatty acids from the saponification of globe thistle oil. In order to provide an amino group donor for the transaminase, at the same time as the addition of the organic phase, 10.7 mL of an alanine solution (125 g/L) were added to the fermentation broth. For the sampling, 2 mL of fermentation broth were removed from the reactor and part of it was diluted 1/20 in an acetone/HCl mixture (c(HCl) =0.1 mol/L) and extracted. Samples were taken from all 8 reactors at 1.25 h, 3 h, 5 h, 20 h, 22 h and 25 h after the start of the biotransformation. The transfer rates for oxygen (OTR=oxygen transfer rate) and carbon (CTR=carbon transfer rate) were determined during the fermentation via offgas analysis on the DasGip systems. The fermentation was ended 22 h after the start of the biotransformation.

Quantification of ALS, ALSME, DDS, DDSME, LS, LSME, HLS, HLSME, OLS and OLSME in fermentation samples was carried out by means of LC-ESI/MS$^2$ by reference to an external calibration for all analytes and using the internal standard aminoundecanoic acid (AUD).

For this purpose, the following instruments were used:
HPLC instrument 1260 (Agilent; Boblingen) with autosampler (G1367E), binary pump (G1312B) and column oven (G1316A)
Mass spectrometer TripelQuad 6410 (Agilent; Boblingen) with ESI source
HPLC column: Kinetex C18, 100×2.1 mm, particle size: 2.6 µm, pore size 100 Å (Phenomenex; Aschaffenburg)
Precolumn: KrudKatcher Ultra HPLC In-Line Filter; 0.5 µm filter depth and 0.004 mm internal diameter (Phenomenex; Aschaffenburg)

The samples were prepared by pipetting 1900 µL of solvent (acetone/0.1 N HCl mixture=1:1) and 100 µL of sample into a 2 mL reaction vessel. The mixture was vortexed for ca. 10 seconds and then centrifuged at ca. 13 000 rpm for 5 min. The clear supernatant was removed using a pipette and analyzed following appropriate dilution with diluent (80% (v/v) ACN, 20% double distilled H$_2$O (v/v), +0.1% formic acid). For each 900 µL sample, 100 µL of ISTD were pipetted in (10 µL for a sample volume of 90 µL).

The HPLC separation was carried out using the aforementioned column or precolumn. The injection volume was 0.7 µL, the column temperature 50° C., the flow rate 0.6 mL/min. The mobile phase consisted of eluent A (0.1% strength (v/v) aqueous formic acid) and eluent B (acetonitrile with 0.1% (v/v) formic acid). The following gradient profile was used

| Time [min] | Eluent A [%] | Eluent B [%] |
|---|---|---|
| 0 | 77 | 23 |
| 0.3 | 77 | 23 |
| 0.4 | 40 | 60 |
| 2.5 | 40 | 60 |
| 2.6 | 2 | 98 |
| 5.5 | 2 | 98 |
| 5.6 | 77 | 23 |
| 9 | 77 | 23 |

The ESI-MS$^2$ analysis was carried out in the positive mode with the following parameters of the ESI source:
Gas temperature 280° C.
Gas flow 11 L/min
Nebulizer pressure 50 psi
Capillary tension 4000 V Detection and quantification of the individual compounds was carried out with the following parameters, with in each case one product ion being used as qualifier and one being used as quantifier:

| Analyte | Precursor ion [m/z] | Product ion [m/z] | Residence time [ms] | Collision energy [eV] |
|---|---|---|---|---|
| DDSME | 245.2 | 167.1 | 25 | 6 |
| DDSME | 245.2 | 149.1 | 50 | 8 |
| HLSME | 231.3 | 181.2 | 15 | 2 |
| HLSME | 231.3 | 163.2 | 25 | 5 |
| DDS | 231.2 | 213.2 | 50 | 0 |
| DDS | 231.2 | 149.1 | 25 | 9 |
| ALSME | 230.3 | 198.1 | 25 | 10 |
| ALSME | 230.3 | 163.2 | 15 | 10 |
| OLSME | 229.2 | 197.2 | 50 | 0 |
| OLSME | 229.2 | 161.1 | 25 | 5 |
| HLS | 217.2 | 181.2 | 35 | 0 |
| HLS | 217.2 | 163.1 | 20 | 4 |
| OLS | 215.2 | 161.2 | 25 | 0 |
| OLS | 215.2 | 95.2 | 60 | 13 |

Results:

If DEHPA as described in the prior art is used as cation exchanger, then directly after adding the compound to the culture, this results in a drop in the OTR. The curve drops within a short time to 0, which indicates that metabolically active cells are no longer present in the culture. DEHPA thus has a high grade toxic effect on cells.

If lauric acid is used as liquid cation exchanger instead of DEHPA, then although this likewise leads to a drop in the OTR, this is not so severe, and in the course of the next 22 h the cells recover and exhibit increasing metabolic activity. Accordingly, lauric acid is notably less toxic than DEHPA.

Even better results can be observed when using saturated fatty acids with longer carbon chains. If palmitic acid and stearic acid are used, then the OTR curve falls significantly more shallowly than in the case of using lauric acid or even DEHPA. It can be concluded from this that these fatty acids have a considerably lower toxic effect.

The use of unsaturated fatty acids such as palmitoleic acid, saponified globe thistle oil (contains predominantly linoleic acid) and oleic acid surprisingly leads to even better results. These fatty acids surprisingly exhibit an even lower toxicity than the saturated fatty acids.

LITERATURE SOURCES

J. Sangster, *Octanol-Water Partition Coefficients: Fundamentals and Physical Chemistry*, Vol. 2 of *Wiley Series in Solution Chemistry*, John Wiley & Sons, Chichester, 1997

Asano, Y., Fukuta, y., Yoshida, Y., and Komeda. H. (2008): The Screening, Characterisation, and Use of w-Laurolactam Hydrolase: A New Enzymatic Synthesis of 12-Aminolauric Acid, *Biosc. Biotechn. Biochem.,* 72 (8), 2141-2150

DE10200710060705 (2007): Recombinant cells producing w-aminocarboxylic acids or their lactams

The invention claimed is:

1. A process for removing an organic compound comprising one or more positive charges from an aqueous solution, the process comprising:
providing the aqueous solution comprising the organic compound and a hydrophobic organic solution comprising a liquid cation exchanger, wherein the liquid cation exchanger is a hydrophobic fatty acid but not a fatty acid ester,
after the providing, contacting the aqueous solution and the hydrophobic organic solution, and
separating off the hydrophobic organic solution from the aqueous solution,
wherein the organic compound comprises at least two amino groups and no negatively charged functional group,
wherein the organic compound is a compound of Formula $H_2N-(CH_2)_x-NH_2$, wherein x is 1 to 20; or wherein the organic compound is a cyclic sugar comprising at least two amino groups, and
wherein the process does not employ a membrane.

2. The process according to claim 1, wherein a temperature of the contacting is from 28 to 70° C.

3. The process according to claim 1, wherein a pH of the contacting is from 6 to 8.

4. The process according to claim 1, wherein a quantitative ratio of the liquid cation exchanger to the organic compound is at least 1.

5. The process according to claim 1, wherein a volume ratio of the hydrophobic organic solution to the aqueous solution is from 1:10 to 10:1.

6. The process according to claim 1, wherein the liquid cation exchanger is a fatty acid comprising more than 12 carbon atoms.

7. The process according to claim 1, wherein the liquid cation exchanger is an unsaturated fatty acid.

8. The process according to claim 1, wherein the aqueous solution further comprises a biological agent having a catalytic activity.

9. The process according to claim 8, wherein the biological agent is a cell.

10. The process according to claim 1, wherein the hydrophobic organic solution further comprises an organic solvent.

* * * * *